United States Patent [19]

Tanaka et al.

[11] Patent Number: 4,500,730

[45] Date of Patent: Feb. 19, 1985

[54] PROCESS FOR PRODUCING AROMATIC POLYCARBOXYLIC ACID

[75] Inventors: Toru Tanaka; Masanori Hataya; Kazuo Tanaka; Yukio Sakai; Yasufumi Hamada, all of Kurashiki, Japan

[73] Assignee: Mitsubishi Gas Chemical Company, Inc., Japan

[21] Appl. No.: 454,982

[22] Filed: Jan. 3, 1983

[30] Foreign Application Priority Data

Jan. 18, 1982 [JP] Japan .................................. 57-5749

[51] Int. Cl.³ .................. C07C 51/235; C07C 51/265
[52] U.S. Cl. ..................................... 562/416; 422/240; 422/241
[58] Field of Search ................. 562/416; 422/240, 241

[56] References Cited

U.S. PATENT DOCUMENTS 4,297,507 10/1981 Komatsu et al. ..................... 562/416
4,346,232  9/1982 Komatsu et al. ..................... 562/416

FOREIGN PATENT DOCUMENTS 0832995  4/1960 United Kingdom ................ 562/416

*Primary Examiner*—Natalie Trousof
*Assistant Examiner*—Patricia M. Scott
*Attorney, Agent, or Firm*—Armstrong, Nikaido, Marmelstein & Kubovcik

[57] ABSTRACT

An aromatic polycarboxylic acid is produced by oxidation of an alkyl-substituted aromatic aldehyde or carboxyLic acid with molecular oxygen in water as a solvent in the presence of bromine ions or further together with heavy metal ions as a catalyst in a reactor using a zirconium material whose surface is coated with an oxide layer as a material of construction. The oxidation can be carried out in high yield without corrosion of the material of construction.

10 Claims, No Drawings

PROCESS FOR PRODUCING AROMATIC POLYCARBOXYLIC ACID

BACKGROUND OT THE INVENTION

The present invention relates to a process for producing an aromatic polycarboxylic acid by oxidizing a corresponding polyalkyl-substituted aromatic aldehyde or a polyalkyl-substituted carboxylic acid in water as a solvent in the presence of a bromine ion-containing catalyst.

Among aromatic polycarboxylic acids, terephthalic acid is used as raw materials for synthetic fibers and synthetic resin, trimellitic acid is widely used as raw materials for alkyd resin, high grade plasticizer and polyester, and pyromellitic acid is used as raw materials for special plasticizer, polyamide and polyimide.

The so far well known processes for producing aromatic polycarboxylic acids include a process for producing terephthalic acid by oxidizing p-xylene with air in an acetic acid as a solvent in the presence of a cobalt-manganese-bromine catalyst, a process for producing trimellitic acid by oxidizing pseudocumene in the same manner as in the said process for producing terephthalic acid, or by oxidizing pseudocumene with nitric acid, and a process for producing pyromellitic acid by oxidizing a polyalkyl-substituted benzene such as durene, trimethylisopropylbenzene, etc. in a gaseous phase or with nitric acid.

As a result of extensive studies of a process for economically producing aromatic polycarboxylic acids such as trimellitic acid, pyromellitic acid, etc., the present inventors found that aromatic polycarboxylic acids could be obtained easily in high yields in one step by oxidizing the corresponding polyalkyl-substituted aromatic aldehydes or polyalkyl-substituted aromatic carboxylic acids with molecular oxygen in water as a solvent in the presence of bromine ions and metal ions of manganese, cerium, etc., as already disclosed in Japanese Patent Application Kokai (Laid-Open) No. 26839/81, but the prior process is an improved advantageous oxidation process free from the disadvantages of the conventional processes, but still has such a disadvantage as a high corrosiveness due to a reaction condition involving bromine ions and molecular oxygen at a high temperature.

On the other hand, Japanese Patent Application Kokai (Laid-Open) No. 125631/79 discloses a process for producing terephthalic acid by oxidizing p-tolualdehyde in water as a solvent in the presence of bromine ions in a reactor using zirconium as a material of construction, which still has a risk of occurrence of corrosion at an elevated reaction temperature, or under an elevated oxygen partial pressure or at an elevated concentration of $Br^-$ as the catalyst, particularly at an elevated HBr concentration, where it has been found that the corrosion is not a general corrosion occurring on the entire surface of liquid-contact parts of the material of construction, but a local corrosion such as pitting corrosion, intercrystalline corrosion, etc.

Generally, the pitting corrosion is characteristic of very small cross-sectional area of corrosion and of corrosion advancing deeply in a material, and thus has such a risk that a pitting hole penetrates a material as the corrosion advances, though the cross-sectional area of corrosion is very small. Particularly in the case of using a corrosion resistant material in a pressure vessel as in the present invention, the ordinary corrosion resistant material having a thickness of several millimeters on average is used as a lining material or cladding material to a low grade substratum material such as carbon steel, and thus occurrence of pitting corrosion must be completely prevented, if a possible accident due to the occurrence and the successive advance of a local corrosion is taken into account.

As a result of further studies of a material for a reactor for producing an aromatic polycarboxylic acid without any risk of such local corrosion and of corrosion tests of zirconium under expected oxidation reaction conditions, the present inventors have found that the occurrence of corrosion can be considerably reduced or prevented by using zirconium whose surface is coated with an oxide layer as a material of construction for the reactor, and have established the present invention.

SUMMARY OF THE INVENTION

The present invention provides a process for producing an aromatic polycarboxylic acid by oxidizing an alkyl-substituted aromatic aldehyde or alkyl-substituted aromatic carboxylic acid with molecular oxygen in water as a solvent in the presence of bromine ions or bromine ions and heavy metal ions as a catalyst, which comprises conducting the oxidation in a reactor using a zirconium material whose surface is coated with an oxide layer as a material of construction.

The zirconium material for use as a material of construction in the present invention is zirconium and zirconium alloys including all so far commercially available zirconium materials and is preferably a zirconium alloy containing at least 96% by weight of zirconium and hafnium in total. The zirconium material is given an oxide layer according to an appropriate method, for example, by heating in air, by chemical oxidation treatment, by heating in hot water, by electrochemical anodic oxidation, etc., and specific examples thereof include:

(i) treatment in a gas containing at least 2% by volume of oxygen at a temperature of 240° to 750° C., preferably 350° to 550° C., for 0.5 to 24 hours, (ii) treatment in an atmosphere adjusted to contain a gas phase under an oxygen partial pressure of 0.1 to 1.5 $kg/cm^2$ in an aqueous solution containing 0.2 to 2% by weight of hydrobromic acid and 1 to 4% by weight of manganese bromide, (iii) treatment in an aqueous solution containing 10 to 61% by weight of nitric acid at a temperature of 100° to 200° C. for 1 to 24 hours, (v) treatment in hot water at 350° C., etc., whereby an oxide layer having a thickness of at least 0.05 $\mu m$, preferably 0.05 to 5 $\mu m$ can be formed on the zirconium material.

It is desirable before the said oxidation treatment to polish the zirconium material in a wet or dry manner, and then wash the material with an organic solvent such as acetone, etc. to remove oily materials therefrom.

The reactor for use in the present invention has the said zirconium material with the said specific composition as a material of construction, and it is not always necessary that the reactor is wholly made from the zirconium material, but it is necessary that at least the inner wall of the reactor has a zirconium material having a thickness large enough to withstand a mechanical erosion.

The alkyl-substituted aromatic aldehyde to be used as the raw material in the oxidation reaction according to the present invention includes p-tolualdehyde, 2,4-dimethylbenzaldehyde, 3,4-dimethylbenzaldehyde, 2,4,5-trimethylbenzaldehyde, 2,4,6-trimethylbenzaldehyde, etc., and the alkyl-substituted aromatic carboxylic acid includes toluic acid, 2,4-dimethylbenzoic acid, 3,4-dimethylbenzoic acid, 2,4,5-trimethylbenzoic acid, 2,4,6-trimethylbenzoic acid, etc. The bromine ion source for use as the catalyst in the present invention includes hydrogen bromide, ethyl bromide, sodium bromide, etc., and also compounds capable of liberating bromine ions under the reaction conditions. The metal ion source for use as the catalyst in the present invention includes compounds of heavy metals such as manganese, cerium, etc. The amount of bromine ions as the catalyst is 0.5 to 12% by weight, preferably 0.5 to 6% by weight on the basis of water as the solvent. The amount of the heavy metal ion as the catalyst is 0.1 to 1.5% by weight on the basis of water as the solvent. Below 0.5% by weight of bromine ions, the amount of the raw material alkyl-substituted aromatic aldehyde or alkyl-substituted aromatic carboxylic acid burnt and decomposed is increased, whereas above 12% by weight the oxidation reaction will be suppressed.

In the present invention, oxidation reaction temperature is 180°–280° C., preferably 200°–260° C. Oxydation reaction pressure is automatically set by keeping the reaction temperature constant generally by evaporation and condensation and refluxing operation of water as the solvent, but it is also possible to keep the oxidation reaction pressure at a desired value by the external heat exchanger. Any pressure can be applied so far as it is within a pressure range in which the reaction solution can be kept in a liquid phase, and usually a pressure 15–60 $kg/cm^2$ gage is used.

The amount of water for use as the solvent in the present invention is at least two parts by weight, preferably 3 to 6 parts by weight, per part by weight of the raw material alkyl-substituted aromatic aldehyde or alkyl-substituted aromatic carboxylic acid.

The oxidation reaction can be carried out batchwise, semi-continously, or continuously.

According to the present invention, an aromatic polycarboxylic acid can be produced in high yield in water as a solvent in the presence of bromine ions as a catalyst without any occurrence of corrosion such as pitting corrosion, etc. on a material of construction for a reactor.

PREFERRED EMBODIMENTS OF THE INVENTION

EXAMPLE 1

Four pure metallic zirconium (purity 99.5 wt%) pieces, each 50 mm long, 15 mm wide and 3 mm thick, were made ready, and their surfaces polished with Emery paper #400 in a wet manner, and then washed with acetone. One of the pieces was heated in the atmosphere in an electric furnace at a temperature of 250° C. for 20 hours to form an oxide layer having a thickness of 0.1 $\mu$m on the surface. Another piece was dipped in an aqueous solution containing 1.5% by weight of hydrobromic acid and 2% by weight of manganese bromide in an autoclave and heated at a temperature of 180° C. under the oxygen partial pressure of 3 $kg/cm^2$ in the gas phase for 2 hours to form an oxide layer having a thickness of 0.05 $\mu$m on the surface. The third piece was heated in an aqueous solution containing 10% by weight of nitric acid at a temperature of 100° C. for 3 hours to form an oxide layer having a thickness of 0.05 $\mu$m on the surface. The remaining piece was used as it was after the said polishing and washing as a control without any treatment.

These four test pieces were dipped in a model reaction mixture consisting of 700 g of water, 300 g of trimellitic acid, 18.63 g of hydrobromic acid, and 3.67 g of manganese bromide in an autoclave, and heated at 220° C. for 7 days, while passing air through the autoclave at a flow rate of 400 l/hr by setting an autoclave pressure to maintain the oxygen partial pressure of 5.2 $kg/cm^2$ in the gas phase. Then, the dipped test pieces were observed to investigate occurrence of pitting corrosion. It was found that only the test piece without the oxidation treatment as the control had slight pitting corrosion.

EXAMPLE 2

In the same manner as in Example 1, 4 pure metallic zirconium (purity 99.5 wt%) pieces were made ready, and their surfaces were polished with Emery paper #400 in a wet manner, and washed with acetone. Then, one of the pieces was heated in the atmosphere in an electric furnace at 350° C. for 3 hours to coat the surface with an oxide layer having a thickness of 0.25 $\mu$m. Another piece was dipped in an aqueous solution containing 1.5% by weight of hydrobromic acid and 2% by weight of manganese bromide in an autoclave and heated at 200° C. under an oxygen partial pressure of 1 $kg/cm^2$ in the gas phase for 6 hours to form an oxide layer having a thickness of 0.06 $\mu$m on the surface. The third piece was heated in an aqueous solution containing 30% by weight of nitric acid at 160° C. for 10 hours to form an oxide layer having a thickness of 0.05 $\mu$m on the surface. The remaining piece was used as it was after the said polishing and washing as a control without any treatment. These 4 test pieces were dipped in a model reaction mixture consisting of 700 g of water, 300 g of trimellitic acid, 23.62 g of hydrobromic acid, and 13.56 g of manganese bromide in an autoclave, and heated at 240° C. for 7 days, while passing air through the autoclave at a flow rate of 400 l/hr by setting an autoclave pressure to maintain the oxygen partial pressure of 4.2 $kg/cm^2$ in the gas phase. Then, the dipped test pieces were observed to investigate occurrence of pitting corrosion. It was found that only the test piece without the oxidation treatment as the control had slight pitting corrosion.

EXAMPLE 3

In the same manner as in Example 1, 4 pure metallic zirconium (purity 99.5 wt%) pieces were made ready, and their surfaces were polsihed with Emery paper #400 in a wet manner and then washed with acetone. Then, one of the pieces was heated in the atmosphere in an electric furnace at 550° C. for one hour to coat the surface with an oxide layer having a thickness of 0.25 $\mu$m. Another piece was dipped in an aqueous solution containing 0.1% by weight of hydrobromic acid and 3.87% by weight of manganese bromide in an autoclave and heated at 240° C. under the oxygen partial pressure of 0.5 $kg/cm^2$ in the gas phase for 100 hours to form an oxide layer having a thickness of 0.08 $\mu$m on the surface. The third piece was heated in an aqueous solution containing 55% by weight of nitric acid at 200° C. for 144 hours to form an oxide layer having a thickness of 0.06 $\mu$m on the surface. The remaining piece was used as it was after the said polishing and washing as a control without any treatment. These 4 test pieces were dipped in a model reaction mixture consisting of 700 g of water, 300 g of trimellitic acid, 33.15 g of hydrobromic acid and 58.59 g of manganese bromide and heated at 260° C. in an autoclave for 7 days while passing air through the autoclave at a flow rate of 400 l/hr by setting the autoclave pressure to maintain the oxygen partial pressure of 3.5 kg/cm$^2$ in the gas phase. The dipped test pieces were observed to investigate occurrence of pitting corrosion. It was found that only the test piece without the oxidation treatment as the control had distinct pitting corrosion.

EXAMPLE 4

In the same manner as in Example 1, 4 zirconium alloy pieces containing 1.6% by weight of Sn were made ready, and their surfaces were polished with Emery paper #400 in a wet manner, and washed with acetone. Then, one of the pieces was heated in the atmosphere in an electric furnace at 400° C. for 12 hours to coat the surface with an oxide layer having a thickness of 0.5 μm. Another piece was dipped in an aqueous solution containing 0.8% by weight of hydrobromic acid and 3% by weight of manganese bromide in an autoclave and heated at 220° C. under the oxygen partial pressure of 1 kg/cm$^2$ in the gas phase for 8 hours to form an oxide layer having a thickness of 0.07 μm on the surface. The third piece was heated in an aqueous solution containing 40% by weight of nitric acid at 180° C. for 70 hours to form an oxide layer having a thickness of 0.06 μm on the surface. The remaining piece was used as it was after the said polishing and washing as a control without any treatment. These 4 pieces were dipped in a model reaction mixture consisting of 700 g of water, 300 g of trimellitic acid, 11.81 g of hydrobromic acid and 13.56 g of manganese bromide and heated at 230° C. in an autoclave for 7 days while passing air through the autoclave at a flow rate of 400 l/hr by setting the autoclave pressure to maintain the oxygen partial pressure of 3.5 kg/cm$^2$ in the gas phase. The dipped test pieces were observed to investigate occurrence of pitting corrosion. It was found that only the test piece without the oxidation treatment as the control had distinct pitting corrosion.

EXAMPLE 5

In the same manner as in Example 1, 4 zirconium alloy pieces containing 2.5% by weight of Nb were made ready, and their surfaces were polished with Emery paper #400 in a wet manner and washed with acetone. Then, one of the pieces was heated in the atmosphere in an electric furnace at 300° C. for 10 hours to form an oxide layer having a thickness of 0.15 μm on the surface. Another piece was dipped in an aqueous solution containing 1.5% by weight of hydrobromic acid and 2% by weight of manganese bromide in an autoclave, and heated at 180° C. under the oxygen partial pressure of 2 kg/cm$^2$ in the gas phase for 4 hours to form an oxide layer having a thickness of 0.05 μm on the surface. The third piece was heated in an aqueous solution containing 20% by weight of nitric acid at 140° C. for 8 hours to form an oxide layer having a thickness of 0.05 μm on the surface. The remaining piece was used as it was after the said polishing and washing as a control without any treatment. These 4 test pieces were dipped in a model reaction mixture consisting of 700 g of water, 300 g of trimellitic acid, 23.62 g of hydrobromic acid and 3.67 g of manganese bromide in an autoclave, and heated at 230° C. for 7 days, while passing air through the autoclave at a flow rate of 400 l/hr by setting the autoclave pressure to maintain the oxygen partial pressure of 3.8 kg/cm$^2$ in the gas phase. The dipped test pieces were observed to investigate occurrence of pitting corrosion. It was found that only the test piece as the control without the oxidation treatment had a slight pitting corrosion.

EXAMPLE 6

In the same manner as in Example 1, 4 pure metallic zirconium (purity 99.5 wt%) pieces were made ready, and their surfaces were polished with Emery paper #400 in a wet manner and washed with acetone. Then, one of the pieces was heated in the atmosphere in an electric furnace at 350° C. for one hour to form an oxide layer having a thickness of 0.25 μm on the surface. Another piece was dipped in an aqueous solution containing 1.5% by weight of hydrobromic acid and 2% by weight of manganese bromide in an autoclave and heated at 200° C. under the oxygen partial pressure of 1.0 kg/cm$^2$ in the gas phase for 6 hours to form an oxide layer having a thickness of 0.06 μm on the surface. The third piece was heated in an aqueous solution containing 30% by weight of nitric acid at 160° C. for 10 hours to form an oxide layer having a thickness of 0.05 μm on the surface. The remaining piece was used as it was after the said polishing and washing as a control without any treatment. These 4 test pieces were dipped in a model reaction mixture consisting of 700 g of water, 300 g of trimellitic acid and 20.8 g of hydrobromic acid in an autoclave and heated at 220° C. for 7 days while passing air through the autoclave at a flow rate of 400 l/hr by setting the autoclave pressure to maintain the oxygen partial pressure of 2.5 kg/cm$^2$ in the gas phase. The dipped test pieces were observed to investigate occurrence of pitting corrosion. It was found that only the test pieces as the control without the oxidation treatment had slight pitting corrosion.

EXAMPLE 7

In the same manner as in Example 1, 4 zirconium alloy pieces containing 1.6% by weight of Sn were made ready, and their surfaces were polished with Emery paper #400 in a wet manner and washed with acetone. Then, one of the pieces was heated in the atmosphere in an electric furnace at 300° C. for 3 hours to form an oxide layer having a thickness of 0.15 μm on the surface. Another piece was dipped in an aqueous solution containing 1.5% by weight of hydrobromic acid and 2% by weight of manganese bromide in an autoclave and heated at 180° C. under the oxygen partial pressure of 2 kg/cm$^2$ in the gas phase for 4 hours to form an oxide layer having a thickness of 0.05 μm on the surface. The third piece was heated in an aqueous solution containing 20% by weight of nitric acid at 120° C. for 6 hours to form an oxide layer having a thickness of 0.05 μm on the surface. The remaining piece was used as it was after the said polishing and washing as a control. These 4 test pieces were dipped in a model reaction mixture consisting of 700 g of water, 300 g of trimellitic acid and 20.8 g of hydrobromic acid in an autoclave and heated at 220° C. for 7 days, while passing air through the autoclave at a flow rate of 400 l/hr by setting the autoclave pressure to maintaining the oxygen partial pressure of 2 kg/cm$^2$ in the gas phase. The dipped test pieces were observed to investigate occurrence of pitting corrosion. It was found that only the test piece as the control without the oxidation treatment had slight pitting corrosion.

What is claimed is:

1. In a process for producing an aromatic polycarboxylic acid by oxidizing an alkyl-substituted aromatic aldehyde or an alkyl-substituted aromatic carboxylic acid with molecular oxygen in water as a solvent in the presence of bromine ions or bromine ions and heavy metal ions as a catalyst, the improvement, which comprises conducting the oxidation in a reactor using a zirconium material whose surface is coated with an oxide layer formed from the zirconium material having a thickness of at least 0.05 μm as a material of construction.

2. The process according to claim 1, wherein the zirconium material is zirconium or zirconium alloys.

3. The process according to claim 2, wherein the zirconium alloy is an alloy containing at least 96% by weight of zirconium and hafnium in total.

4. The process according to claim 1, wherein the oxide layer on the zirconium material is an oxide layer formed by heating in air, chemical oxidation, heating in hot water or electrochemical anodic oxidation.

5. The process according to claim 1, wherein the oxide layer is formed by treating the zirconium material with a gas containing at least 2% by volume of oxygen at a temperature of 240° to 750° C. for 0.5 to 24 hours.

6. The process according to claim 1, wherein the oxide layer is formed by treating the zirconium material with an atmosphere containing a gas phase under an oxygen partial pressure of 0.1 to 1.5 kg/cm$^2$ in an aqueous solution containing 0.2 to 2% by weight of hydrobromic acid and 1 to 4% by weight of manganese bromide.

7. The process according to claim 1, wherein the oxide layer is formed by treating the zirconium material with hot water at 350° C.

8. In a process for producing an aromatic polycarboxylic acid by oxidizing an alkyl-substituted aromatic aldehyde or an alkyl-substituted aromatic carboxylic acid with molecular oxygen in water as a solvent in the presence of bromine ions or bromine ions and heavy metal ions as a catalyst, the improvement which comprises conducting the oxidation in a reactor using a zirconium material whose surface is coated with an oxide layer formed from the zirconium material having a thickness of at least 0.05 μm as a material of construction, wherein the oxide layer is formed by treating the zirconium material with an aqueous solution containing 10 to 61% by weight of nitric acid at a temperature of 100° to 200° C. for 1 to 24 hours.

9. The process according to claim 8, wherein the zirconium material is zirconium or zirconium alloys.

10. The process according to claim 9, wherein the zirconium alloy is an alloy containing at least 96% by zirconium and hafnium in total.

* * * * *